(12) United States Patent
Venkata et al.

(10) Patent No.: US 9,079,921 B2
(45) Date of Patent: Jul. 14, 2015

(54) PROCESSES FOR PREPARATION OF EVEROLIMUS AND INTERMEDIATES THEREOF

(75) Inventors: Srinivas Pullela Venkata, Hyderabad (IN); Ganesh Ekambaram, Chennai (IN); Kiran Kumar Kothakonda, Bangalore (IN); Anegondi Sreenivasa Prasad, Hyderabad (IN)

(73) Assignee: Biocon Limited (IN)

( * ) Notice: Subject to any disclaimer, the term of this patent is extended or adjusted under 35 U.S.C. 154(b) by 0 days.

(21) Appl. No.: 13/988,265

(22) PCT Filed: Nov. 17, 2011

(86) PCT No.: PCT/IB2011/055156
§ 371 (c)(1), (2), (4) Date: May 17, 2013

(87) PCT Pub. No.: WO2012/066502
PCT Pub. Date: May 24, 2012

(65) Prior Publication Data
US 2013/0225823 A1   Aug. 29, 2013

(30) Foreign Application Priority Data
Nov. 19, 2010   (IN) .......................... 3485/CHE/2010

(51) Int. Cl.
*C07D 491/00* (2006.01)
*A61K 31/44* (2006.01)
*C07D 498/16* (2006.01)
*C07D 498/18* (2006.01)
*C07F 7/18* (2006.01)

(52) U.S. Cl.
CPC ............ *C07D 498/16* (2013.01); *C07D 498/18* (2013.01); *C07F 7/188* (2013.01)

(58) Field of Classification Search
None
See application file for complete search history.

(56) References Cited

U.S. PATENT DOCUMENTS 5,665,772 A   9/1997  Cottens et al.
7,297,703 B2  11/2007 Navarro et al.

FOREIGN PATENT DOCUMENTS

WO   9409010 A1 * 9/1993
WO   9409010      4/1994

OTHER PUBLICATIONS

International Search Report, Feb. 24, 2012, from International Application No. PCT/IB2011/055156, 2 pages.

* cited by examiner

*Primary Examiner* — Heidi Reese
(74) *Attorney, Agent, or Firm* — Schwegman Lundberg & Woessner, P.A.

(57) ABSTRACT

The present disclosure discloses processes of Everolimus and intermediates: reacting Sirolimus (Rapamycin) under solvent free conditions with appropriate side chain implying portion wise additions, one pot conversion, and resin mediated synthesis.

18 Claims, 2 Drawing Sheets

PROCESSES FOR PREPARATION OF EVEROLIMUS AND INTERMEDIATES THEREOF

FIELD OF THE INVENTION

The present disclosure discloses processes of Everolimus and intermediates: reacting Sirolimus (Rapamycin) under solvent free conditions with appropriate side chain implying portion wise additions, one pot conversion and resin mediated synthesis.

BACKGROUND OF THE INVENTION

Everolimus (RAD-001) (FIG. 1) is an immunosuppressant semi-synthetic drug, marketed by Novartis under the trade names of Zortress® (USA) and Certican® (Europe and other countries) as transplantation medicine and as Afinitor® in oncology. Everolimus is a derivative of Sirolimus (Rapamycin), works similarly to Sirolimus as an mTOR (mammalian target of rapamycin) inhibitor. It is mainly used as an immunosuppressant to prevent rejection in organ transplantation. Everolimus is also used in drug-eluting coronary stents as an immunosuppressant to prevent restenosis. Structurally, Everolimus is 40-O-(2-Hydroxy)ethyl rapamycin. FDA has approved Everolimus in March 2009 for the treatment of advanced kidney cancer, and for the organ rejection prophylaxis in April 2010.

The structure and synthesis of Everolimus [40-O-(2-Hydroxy)ethyl rapamycin] and its use as an immunosuppressant was first described in U.S. Pat. No. 5,665,772 along with other novel Rapamycin derivatives. For the synthesis, firstly Ramapycin and 2-(t-butyldimethylsilyl)oxyethyl triflate are reacted in presence of 2,6-Lutidine in toluene at around 60° C. to obtain corresponding 40-O-[2-(t-butyldimethylsilyl)oxy]ethyl rapamycin, which then converted into Everolimus [40-O-(2-Hydroxy)ethyl rapamycin]. However, the conversion resulted in very poor overall yield.

U.S. Pat. No. 7,297,703 B2 disclosed the use of antioxidant such as 2,6-di-tert-butyl-4-methylphenol for improving the stability of poly-ene macrolides. U.S. Pat. No. 7,297,703 B2 also disclosed substantially pure crystalline polymorph of Everolimus having m.p. 146.5° C. For that amorphous Everolimus is converted into the crystalline form using ethyl acetate and heptane solvents. It is also mentioned that the crystalline form is non-solvate form.

SUMMARY OF THE INVENTION

Accordingly, the present disclosure relates to a process for obtaining Everolimus, said process comprising acts of a) adding 2-(-t-butyldimethylsilyl)oxyethyl triflate (2) to Sirolimus to obtain crude 40-O-[2-(t-butyldimethylsilyl)oxy]ethyl rapamycin (3) and b) treating and purifying the crude 40-O-[2-(t-butyldimethylsilyl)oxy]ethyl rapamycin (3) to obtain Everolimus; a process for obtaining Everolimus, said process comprising acts of a) adding Sirolimus to 2-(-t-butyldimethylsilyl)oxyethyl triflate (2) to obtain crude 40-O-[2-(t-butyldimethylsilyl)oxy]ethyl rapamycin (3) and b) treating and purifying the crude 40-O-[2-(t-butyldimethylsilyl)oxy]ethyl rapamycin (3) to obtain Everolimus; a process for obtaining Everolimus, said process comprising acts of a) obtaining a mixture comprising Sirolimus, 2-(t-butyldimethylsilyl)ethylene glycol (1), base and organic solvent, in any order thereof, b) adding 2-(-t-butyldimethylsilyl)oxyethyl triflate (2) to the mixture to obtain crude 40-O-[2-(t-butyldimethylsilyl)oxy]ethyl rapamycin (3) and c) treating and purifying the crude 40-O-[2-(t-butyldimethylsilyl)oxy]ethyl rapamycin (3) to obtain Everolimus; and a process for obtaining Everolimus, said process comprising acts of a) obtaining a mixture comprising 2-(-t-butyldimethylsilyl)oxyethyl triflate (2), 2-(t-butyldimethylsilyl)ethylene glycol (1), base and organic solvent, in any order thereof, b) adding Sirolimus to the mixture to obtain crude 40-O-[2-(t-butyldimethylsilyl)oxy]ethyl rapamycin (3) and c) treating and purifying the crude 40-O-[2-(t-butyldimethylsilyl)oxy]ethyl rapamycin (3) to obtain Everolimus.

In order that the disclosure may be readily understood and put into practical effect, reference will now be made to exemplary embodiments as illustrated with reference to the accompanying figures. The figure together with a detailed description below, are incorporated in and form part of the specification, and serve to further illustrate the embodiments and explain various principles and advantages, in accordance with the present disclosure where:

DETAILED DESCRIPTION OF THE PREFERRED EMBODIMENTS

Figure 1:
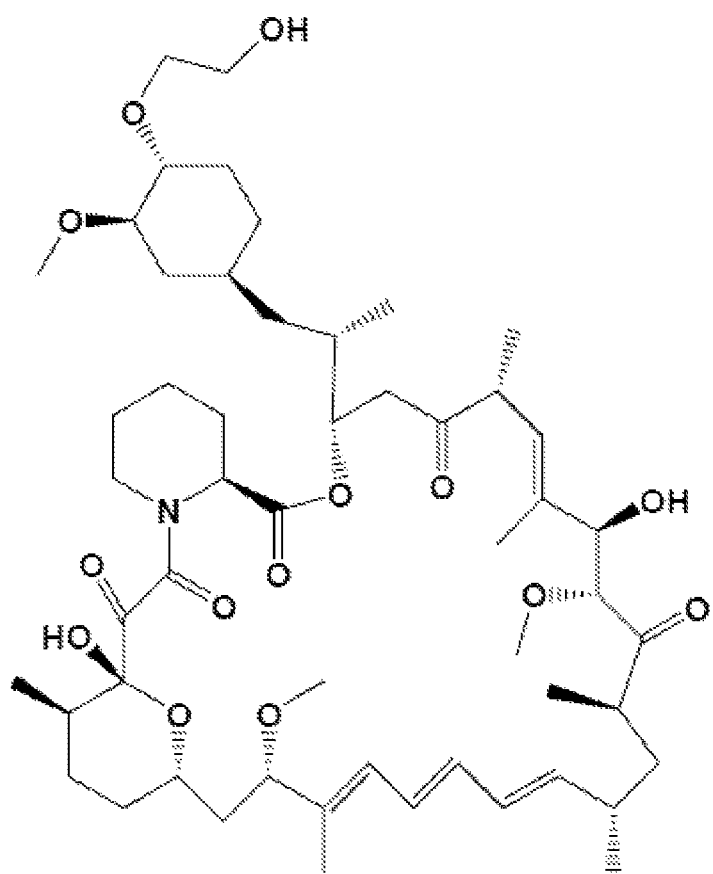
FIG. 1 shows Everolimus an immunosuppressant semi-synthetic drug (Prior art).

The present disclosure relates to a process for obtaining Everolimus, said process comprising acts of:
a) adding 2-(-t-butyldimethylsilyl)oxyethyl triflate (2) to Sirolimus to obtain crude 40-O-[2-(t-butyldimethylsilyl)oxy]ethyl rapamycin (3); and
b) treating and purifying the crude 40-O-[2-(t-butyldimethylsilyl)oxy]ethyl rapamycin (3) to obtain Everolimus.

The present disclosure also relates to a process for obtaining Everolimus, said process comprising acts of:
a) adding Sirolimus to 2-(-t-butyldimethylsilyl)oxyethyl triflate (2) to obtain crude 40-O-[2-(t-butyldimethylsilyl)oxy]ethyl rapamycin (3); and
b) treating and purifying the crude 40-O-[2-(t-butyldimethylsilyl)oxy]ethyl rapamycin (3) to obtain Everolimus.

The present disclosure also relates to a process for obtaining Everolimus, said process comprising acts of:
a) obtaining a mixture comprising Sirolimus, 2-(t-butyldimethylsilyl)ethylene glycol (1), base and organic solvent, in any order thereof;
b) adding 2-(-t-butyldimethylsilyl)oxyethyl triflate (2) to the mixture to obtain crude 40-O-[2-(t-butyldimethylsilyl)oxy]ethyl rapamycin (3); and
c) treating and purifying the crude 40-O-[2-(t-butyldimethylsilyl)oxy]ethyl rapamycin (3) to obtain Everolimus.

The present disclosure also relates to a process for obtaining Everolimus, said process comprising acts of:
a) obtaining a mixture comprising 2-(-t-butyldimethylsilyl)oxyethyl triflate (2), 2-(t-butyldimethylsilyl)ethylene glycol (1), base and organic solvent, in any order thereof;
b) adding Sirolimus to the mixture to obtain crude 40-O-[2-(t-butyldimethylsilyl)oxy]ethyl rapamycin (3); and
c) treating and purifying the crude 40-O-[2-(t-butyldimethylsilyl)oxy]ethyl rapamycin (3) to obtain Everolimus.

In an embodiment of the present disclosure, wherein the 2-(-t-butyldimethylsilyl)oxyethyl triflate (2) is added in complete or portionwise, preferably in about 1.0 to about 10.0 portions, more preferably in about 3.0 to about 5.0 portions.

In another embodiment of the present disclosure, the Sirolimus is added in complete or portionwise, optionally in 1.0 to 10.0 portions, preferably in 3.0 to 5.0 portions.

In yet another embodiment of the present disclosure, the 2-(-t-butyldimethylsilyl)oxyethyl triflate (2) is ranging from about 1 equivalent to about 35 equivalents, preferably about 2 equivalents to about 30 equivalents, more preferably about 4 equivalents to about 22 equivalents; and the Sirolimus is ranging from about 0.1 equivalent to about 1.0 equivalent.

In still another embodiment of the present disclosure, the Sirolimus is in form of solid or solution.

In still another embodiment of the present disclosure, the solid Sirolimus is added in amount ranging from about 25 mg to about 5 kg.

In still another embodiment of the present disclosure, the solution Sirolimus is added in amount ranging from about 25 ml to about 5.0 lts.

In still another embodiment of the present disclosure, said process is carried out at temperature ranging from about −80° C. to about 70° C., preferably from about −70° C. to about 55° C., more preferably from about −45° C. to about 45° C.

In still another embodiment of the present disclosure, said process is carried out at time period ranging from about 5 minutes to about 24 hours, preferably from about 15 minutes to about 12 hours, more preferably from about 30 minutes to about 8 hours.

In still another embodiment of the present disclosure, the treating is carried out using methanol and cationic resin selected from group comprising SK110, UBK558 and T42H or lewis acid selected from group comprising BF3. Et20 and Zinc chroride; and organic acids selected from group comprising methanesulfonic acid, p-toluene sulfonic acid, Formic acid and dihydrochloric acid or any combination thereof.

In still another embodiment of the present disclosure, the purifying is carried out using chromatography or lyophilisation.

In still another embodiment of the present disclosure, the base is organic base selected from group comprising 2,6-Lutidine, pyridine, triethylamine, diisopropylamine, and diisopropylethylamine in amount ranging from about 2.0 eq to about 5.0 eq.

In still another embodiment of the present disclosure, the solvent is organic solvent selected from group comprising Toluene, ethylacetate, Diisopropyl ether and halogenated solvent selected from group comprising dichloromethane and chloroform, or any combination thereof.

In still another embodiment of the present disclosure, the Everolimus has purity ranging from about 85% to about 99.9%, preferably from about 90% to about 99.5%, more preferably from about 98% to about 99.2%.

In still another embodiment of the present disclosure, the Everolimus has yield ranging from about 75% to about 99%, preferably from about 80% to about 98%, more preferably from about 85% to about 95%.

The present disclosure also discloses preparation processes of Everolimus: reacting Sirolimus (Rapamycin) under solvent free conditions with appropriate side chain implying portion wise additions, one pot conversion, and final resin mediated synthesis.

Surprisingly, treatment of 2-(-t-butyldimethylsilyl)oxyethyl triflate (2) with solid Sirolimus under the solvent free conditions produced corresponding 40-O-[2-(t-butyldimethylsilyl)oxy]ethyl rapamycin (3) in reasonably good yield.

Figure 2:
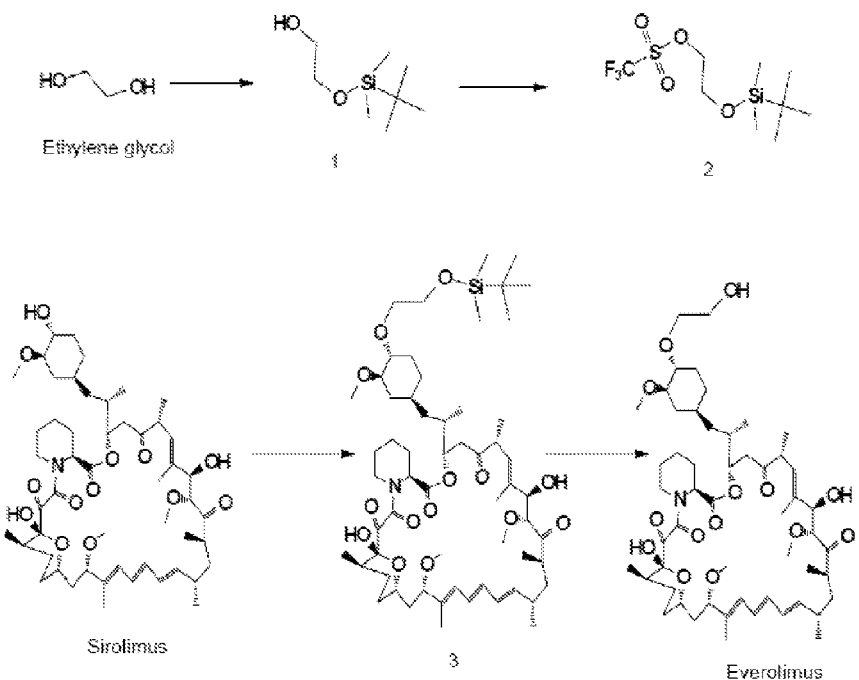
FIG. 2 shows preparation processes of Everolimus and intermediates.

Further modification of the reaction conditions, such as the portion wise addition of the 2-(-t-butyldimethylsilyl)oxyethyl triflate (2) to the solid sirolimus and/or vice versa produced the corresponding product 3 in improved yields and reactions conditions. Addition of the 2-(-t-butyldimethylsilyl)oxyethyl triflate (2) mixture directly to the solid Sirolimus is similar to solid phase and reverse addition techniques, which are very familiar in the synthetic chemistry (FIG. 2).

More interestingly, direct addition of triflic anhydride to the mixture of Sirolimus, 2-(t-butyldimethylsilyl)ethylene glycol (1), and a base such as 2,6-Lutidine in an organic solvent such as dichloromethane under one pot condition produced the corresponding 40-O-[2-(t-butyldimethylsilyl)oxy]ethyl rapamycin (3). The final deprotection of t -butyldimethylsilyl ether of 40-O-[2-(t-butyldimethylsilyl)oxy]ethyl rapamycin (3) is achieved using acidic resin to produce Everolimus in excellent conversion (>90%) overall. The present disclosure discloses the preparation processes of Everolimus and intermediates using most efficient one pot, the solvent free, portion wise addition, reverse addition, solid phase, and resin mediated techniques of process chemistry.

Figure 3:
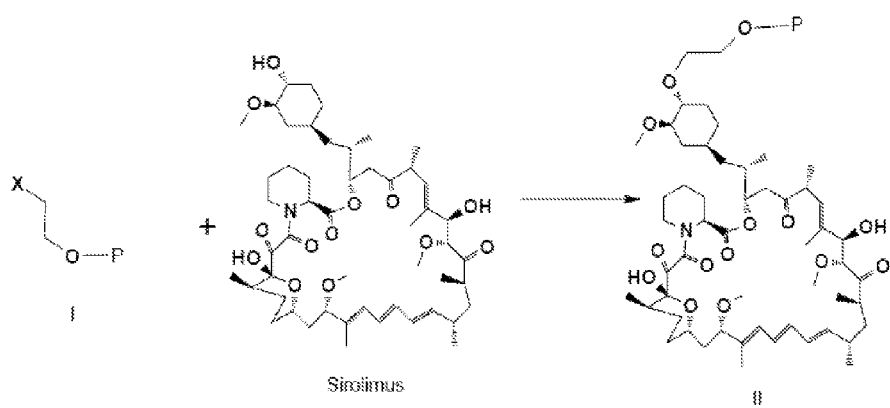
FIG. 3 shows preparation of Everolimus intermediate 40-O-[2-(t-butyldimethylsilyl)oxy]ethyl rapamycin (3).

According to the depicted embodiments of the present disclosure, Everolimus intermediate 40-O-[2-(t-butyldimethylsilyl)oxy]ethyl rapamycin (3) is prepared by following FIG. 3.

In FIG. 3, particularly in structure I, X=leaving group, P=protecting group.

More precisely, X=sulfonate (triflate, mesylate, tosylate) or halogen (chlorine, bromine, iodine); P=silyl protecting group (TMS, TES, TIPS, TBDMS, TBDPS).

According to the depicted embodiments of the present disclosure, Everolimus intermediate 40-O-[2-(t-butyldimethylsilyl)oxy]ethyl rapamycin (3) is prepared by following (where in X=O-trifate and P=O-TBDMS):

i) complete/portion wise addition of the 2-(-t-butyldimethylsilyl)oxyethyl triflate (2) to Sirolimus solid/solution.

ii) complete/portion wise addition of the 2-(-t-butyldimethylsilyl)oxyethyl triflate (2) containing a base such as 2,6-Lutidine, and an organic solvent such as dichloromethane to solid Sirolimus solid/solution.

iii) complete/portion wise addition of the Sirolimus solid/solution to the 2-(-t-butyldimethylsilyl)oxyethyl triflate (2).

iv) complete/portion wise addition of the Sirolimus solid/solution to the 2-(-t-butyldimethylsilyl)oxyethyl triflate (2) containing a base such as 2,6-Lutidine, and an organic solvent such as dichloromethane, Ethylacetate, Toluene etc.

v) complete/portion wise addition of triflic anhydride to the mixtrure of Sirolimus, 2-(t-butyldimethylsilyl)ethylene glycol (1), and a base such as 2,6-Lutidine in an organic solvent such as dichloromethane under one pot condition.

The most preferred base is 2,6-Lutidine; more preferred base is any organic base such as pyridine, triethylamine, diisopropylamine, diisopropylethylamine, etc.;

The most preferred solvent is dichloromethane; more preferred solvent is any halogenated solvent such as dichloromethane, chloroform, carbon tetrachloride, etc.; preferred solvent is any organic solvent, and mixture thereof.

The temperature range for the process is preferably from −80° C. to 70° C.; more preferably from −70° C. to 55° C.; most preferably from −45° C. to 45° C.

The equivalents of 2-(-t-butyldimethylsilyl)oxyethyl triflate (2) is preferably from 1 to 35, more preferably from 2 to 30, most preferably from 4 to 22.

The reaction time is preferably from 5 minutes to 24 h, more preferably 15 minutes to 12 h, most preferably 0.5 h to 8 h.

According to the depicted embodiments of the present disclosure, Evelorimus is synthesized by cleaving the silyl protecting of structure II of FIG. 3, for instance 40-O-[2-(t-butyldimethylsilyl)oxy]ethyl rapamycin (3) by a cationic resin such as SK110, UBK558, T42H or by lewis acid such as $BF_3 \cdot Et_2O$, Zinc chloride etc.

According to the depicted embodiments of the present disclosure, pure Everolimus is isolated by HPLC and lyophilisation.

The present disclosure is further elaborated by the following examples and figures. However, these examples should not be construed to limit the scope of the disclosure.

EXAMPLES

Example 1

40-O-[2-(t-butyldimethylsilyl)oxy]ethyl rapamycin (3)

To the solid Sirolimus (25 g), is added freshly prepared solution of 2-(-t-butyldimethylsilyl)oxyethyl triflate (2) (4 eq) in 2,6-Lutidine (2 eq), and dichloromethane (3.0 vol) at room temperature. The resulting mixture is stirred till completion of the reaction, quenched, and the organic layer is separated. The resulting organic layer is purified to obtain corresponding 40-O-[2-(t-butyldimethylsilyl)oxy]ethyl rapamycin (3) in 35% yield.

Example 2

40-O-[2-(t-butyldimethylsilyl)oxy]ethyl rapamycin (3)

To the mixture of Sirolmus (25 g) (1 eq), 2-(t-butyldimethylsilyl)ethylene glycol (5 eq), 2,6-Lutidine (2.2 eq) in dichloromethane (3 vol) in one pot condition, is added triflic anhydride (5 eq) and stirred. After the completion of the reaction, the crude product is isolated by chromatographic purification as a syrup in more than 30% yield.

Example 3

40-O-[2-(t-butyldimethylsilyl)oxy]ethyl rapamycin (3)

To the solution of 2-(-t-butyldimethylsilyl) oxyethyl triflate (2) (4 eq) in 2,6-Lutidine (2 eq), and dichloromethane (3 vol), is added solid Sirolimus (25 g). The resulting mixture is stirred till completion of the reaction, quenched, and separated the organic layer. The resulting organic layer is purified to obtain corresponding 40-O-[2-(t-butyldimethylsilyl)oxy]ethyl rapamycin (3) in 45% yield.

Example 4

40-O-[2-(t-butyldimethylsilyl)oxy]ethyl rapamycin (3)

To the solution of 2-(-t-butyldimethylsilyl)oxyethyl triflate (2) (4 eq) in 2,6-Lutidine (2 eq), and Ethyl acetate (3 vol), is added solid Sirolimus (25 g). The resulting mixture is stirred at 45-50° C. till completion of the reaction, quenched, and organic layer is separated. The resulting organic layer is purified to obtain corresponding 40-O-[2-(t-butyldimethylsilyl)oxy]ethyl rapamycin (3) in 35% yield.

Example 5

40-O-[2-(t-butyldimethylsilyl)oxy]ethyl rapamycin (3)

To the solution of 2-(-t-butyldimethylsilyl)oxyethyl triflate (2) (4 eq) in 2,6-Lutidine (2 eq), and dichloromethane (3 vol), is added solid Sirolimus (25 g). The resulting mixture is stirred till completion of the reaction, quenched, and organic layer is separated. The resulting organic layer is purified to obtain corresponding 40-O-[2-(t-butyldimethylsilyl)oxy]ethyl rapamycin (3) in 45% yield.

Example 6

40-O-[2-(t-butyldimethylsilyl)oxy]ethyl rapamycin (3)

To the solution of 2-(-t-butyldimethylsilyl)oxyethyl triflate (2) (4 eq) in 2,6-Lutidine (2 eq), and Toluene (3 vol), is added solid Sirolimus (25 g). The resulting mixture is stirred till completion of the reaction, quenched, and organic layer is separated. The resulting organic layer is purified to obtain corresponding 40-O-[2-(t-butyldimethylsilyl)oxy]ethyl rapamycin (3) in 30% yield.

Example 7

40-O-[2-(t-butyldimethylsilyl)oxy]ethyl rapamycin (3)

To the solution of 2-(-t-butyldimethylsilyl)oxyethyl triflate (2) (4 eq) in 2,6-Lutidine (2 eq), and dichloromethane (3 vol), is added solid Sirolimus (25 g). The resulting mixture is stirred till completion of the reaction, quenched, and organic layer is separated. The resulting organic layer is purified to obtain corresponding 40-O-[2-(t-butyldimethylsilyl)oxy]ethyl rapamycin (3) in 45% yield.

Example 8

40-O-[2-(t-butyldimethylsilyl)oxy]ethyl rapamycin (3)

To the solution of 2-(-t-butyldimethylsilyl)oxyethyl triflate (2) (8 eq) in 2,6-Lutidine (3.0 eq), and dichloromethane (3 vol), is added solid Sirolimus (25 g). The resulting mixture is stirred till completion of the reaction, quenched, and organic layer is separated. The resulting organic layer is purified to obtain corresponding 40-O-[2-(t-butyldimethylsilyl)oxy]ethyl rapamycin (3) in 40% yield.

Example 9

40-O-[2-(t-butyldimethylsilyl)oxy]ethyl rapamycin (3)

To the solution of 2-(-t-butyldimethylsilyl)oxyethyl triflate (2) (8 eq) in 2,6-Lutidine (3.0 eq), and dichloromethane (3 vol), is added in three portions to solid Sirolimus (25 g). The resulting mixture is stirred till completion of the reaction, quenched, and organic layer is separated. The resulting organic layer is purified to obtain corresponding 40-O-[2-(t-butyldimethylsilyl)oxy]ethyl rapamycin (3) in 50% yield.

Example 10

40-O-[2-(t-butyldimethylsilyl)oxy]ethyl rapamycin
(3)

To a solution of Sirolimus (25 g) in Dichloromethane (25 ml), is added a freshly prepared solution of 2-(-t-butyldimethylsilyl)oxyethyl triflate (2) (4 eq) in 2,6-Lutidine (3.0 eq), and dichloromethane (3.0 vol) at room temperature. The resulting mixture is stirred at reflux temperature till completion of the reaction, quenched, and organic layer is separated. The resulting organic layer is purified to obtain corresponding 40-O-[2-(t-butyldimethylsilyl)oxy]ethyl rapamycin (3) in 25% yield.

Example 11

40-O-[2-(t-butyldimethylsilyl)oxy]ethyl rapamycin
(3)

To the solid Sirolimus (25 g), is added freshly prepared solution of 2-(-t-butyldimethylsilyl)oxyethyl triflate (2) (4.0 eq) in 2,6-Lutidine (2.5 eq), and dichloromethane (3.0 vol) at room temperature. The resulting mixture is stirred till completion of the reaction, quenched, and organic layer is separated. The resulting organic layer is purified to obtain corresponding 40-O-[2-(t-butyldimethylsilyl)oxy]ethyl rapamycin (3) in 35% yield.

Example 12

40-O-[2-(t-butyldimethylsilyl)oxy]ethyl rapamycin
(3)

To the solid Sirolimus (25 g), is added freshly prepared solution of 2-(-t-butyldimethylsilyl)oxyethyl triflate (2) (8.0 eq) and 2,6-Lutidine (3.0 eq), and dichloromethane (3.0 vol) at room temperature in five lots. The resulting mixture is stirred till completion of the reaction, quenched, and organic layer is separated. The resulting organic layer is purified to obtain corresponding 40-O-[2-(t-butyldimethylsilyl)oxy]ethyl rapamycin (3) in 40% yield.

Example 13

40-O-[2-(t-butyldimethylsilyl)oxy]ethyl rapamycin
(3)

To the solution of 2-(-t-butyldimethylsilyl)oxyethyl triflate (2) (8 eq) in 2,6-Lutidine (3.0 eq), and dichloromethane (3 vol), is added in three portions to three lots of solid Sirolimus (each lot 5.0 g) (25 g). The resulting mixture is stirred till completion of the reaction, quenched, and separated the organic layer. The resulting organic layer is purified to obtain corresponding 40-O-[2-(t-butyldimethylsilyl)oxy]ethyl rapamycin (3) in 50% yield.

Example 14

40-O-(2-Hydroxy)ethyl rapamycin

To the solution of 40-O-[2-(t-butyldimethylsilyl)oxy]ethyl rapamycin (3) (30 g) in methanol (5 vol), is added cationic resin (10% wt/wt) and stirred till the completion of the reaction. Pure product (Everolimus) having about 99.2% purity is isolated from the crude by HPLC purification in >90% yield.

Example 15

40-O-[2-(t-butyldimethylsilyl)oxy]ethyl rapamycin
(3)

To the solution of 2-(t-butyldimethysilyloxy)ethyl triflate (2) (8.0 eq) in 2,6-lutidine (2.5 eq) and Dichloromethane (2.0 vol) is added Solid Sirolimus (5.0 kg). The resulting mixture is stirred till completion of the reaction, quenched and the organic layer is separated. The crude product is isolated by chromatographic purification to get pure 40-O-[2-(t-butyldimethylsilyl)oxy]ethyl rapamycin (3) as foam in 45% yield.

Example 16

40-[O-[2-(t-butyldimethylsilyl)oxy]ethyl rapamycin
(3)]

To the solution of 40-[O-[2-(t-butyldimethylsilyl)oxy] ethyl rapamycin (3) (2.25 kg) in methanol (10 vol) is added 1.0 N HCl (2.0 vol).and stirred till completion of the reaction. After reaction completion the reaction mass is partitioned between water and ethylacetate. The organic layer is dried over Sodium Sulphate and evaporated under reduced pressure dryness which is further purified by HPLC purification to get pure Everolimus as a white solid (300-350g) with purity more than 98% in greater than 85% yield.

Example 17

The crude of everolimus from the synthetic process diluted with acetonitrile filtered through 0.45μ membrane and loaded on a C18 reverse phase chromatography column. The column is eluted under isocratic conditions with acetonitrile and buffer in the ratio of 55:45. During elution, fractions are collected. The fractions with desired purity are combined, diluted with water, and extracted with ethyl acetate. This organic layer with the purified product is then concentrated under vacuum. The concentrated foam is diluted with ethyl acetate and hexane. This solution is passed through a normal phase silica column, which is pre-equilibrated with 45% ethyl acetate in n-hexane. The resin is washed and eluted with 70% ethyl acetate in a gradient manner. The product-containing elute is collected and analyzed for purity by HPLC. The desired purity pool is concentrated under vacuum. The chromatographic purity is 99.67% wherein isomer C is at range of 0.19% and sirolimus at 0.08% is observed.

Example 18

The crude of everolimus from the synthetic process diluted with acetone filtered through 0.45μ membrane and loaded on a C18 reverse phase chromatography column. The column is eluted under isocratic conditions with acetone and water at the ratio of 45:55. During elution, fractions are collected. The fractions with desired purity are combined, diluted with water, and extracted with butyl acetate. This organic layer with the purified product is then concentrated under vacuum. The concentrated foam is diluted with ethyl acetate and heptane. This solution is passed through a normal phase silica column, which is pre-equilibrated with 55% butyl acetate in n-hexane. The resin is washed and eluted with 80% ethyl acetate in a gradient manner. The product-containing elute is collected and analyzed for purity by HPLC. The desired purity pool is concentrated under vacuum. The chromatographic purity is 98. 9%, with sirolimus content less than 0.3% and isomer C content less 0.3%.

Example 19

The crude of everolimus from the synthetic process diluted with methanol filtered through 0.45μ membrane and loaded on a C18 reverse phase chromatography column. The column is eluted under gradient conditions with methanol and water at the ratio of 25:75 to 65:35. During elution, fractions are collected. The fractions with desired purity are combined, diluted with water, and extracted with methyl, tertiary-butyl ether. This organic layer with the purified product is then concentrated under vacuum. The concentrated foam is diluted with methyl, tertiary-butyl ether and hexane. This solution is passed through a normal phase silica column, which is pre-equilibrated with 35% methyl, t-butyl ether in n-hexane. The resin is washed and eluted with 80% ethyl acetate in a gradient manner. The product-containing elute is collected and analyzed for purity by HPLC. The desired purity pool is concentrated under vacuum. The chromatographic purity is 98.8%; with sirolimus content less than 0.3% and isomer C content less than 0.5%

We claim:
1. A process for obtaining Everolimus, said process comprising:
  a) adding 2-(t-butyldimethylsilyl)oxyethyl triflate to Sirolimus to obtain crude 40-O-[2-(t-butyldimethylsilyl)oxy]ethyl rapamycin;
  b) treating the crude 40-O-[2-(t-butyldimethylsilyl)oxy] ethyl rapamycin to obtain Everolimus; and
  c) purifying the Everolimus;
wherein said treating comprises treating crude 40-O-[2-(t-butyldimethylsilyl)oxy]ethyl rapamycin with methanol and a cationic resin; a Lewis acid; an organic acid, or any combination thereof.
2. A process for obtaining Everolimus, said process comprising:
  a) obtaining a mixture comprising Sirolimus, 2-(t-butyldimethylsilyl)ethylene glycol, base and organic solvent;
  b) adding triflic anhydride to the mixture to obtain crude 40-O-[2-(t-butyldimethylsilyl)oxy]ethyl rapamycin;
  c) treating the crude 40-O-[2-(t-butyldimethylsilyl)oxy] ethyl rapamycin to obtain Everolimus; and
  d) purifying the Everolimus.
3. A process for obtaining Everolimus, said process comprising:
  a) obtaining a mixture comprising triflic anhydride, 2-(t-butyldimethylsilyl) ethylene glycol, base and organic solvent;
  b) adding Sirolimus to the mixture to obtain crude 40-O-[2-(t-butyldimethylsilyl)oxy]ethyl rapamycin;
  c) treating the crude 40-O-[2-(t-butyldimethylsilyl)oxy] ethyl rapamycin to obtain Everolimus; and
  d) purifying the Everolimus.
4. The process as claimed in claim 1, wherein the 2-(t-butyldimethylsilyl)oxyethyl triflate is added in complete or in about 1.0 to about 10.0 portions.
5. The process as claimed in claim 3, wherein the Sirolimus is added in complete or in 1.0 to 10.0 portions.
6. The process as claimed in claim 1, wherein the adding comprises adding from about 1 equivalent to about 35 equivalents of 2-(t-butyldimethylsilyl)oxyethyl triflate.
7. The process as claimed in claim 1, wherein the Sirolimus is in form of solid or solution; and wherein the Sirolimus is ranging from about 0.1 equivalent to about 1.0 equivalent.
8. The process as claimed in claim 7, wherein the solid Sirolimus is in amount ranging from about 25 mg to about 5 kg.
9. The process as claimed in claim 7, wherein the solution Sirolimus is in amount ranging from about 25 mL to about 5.0 L.
10. The process as claimed in claim 1, wherein said process is carried out at temperature ranging from about −80° C. to about 70° C.
11. The process as claimed in claim 1, wherein said process is carried out at time period ranging from about 5 minutes to about 24 hours.
12. The process as claimed in claim 1, wherein the purifying chromatographing or lyophilizing the Everolimus.
13. The process as claimed in claim 2, wherein the base is organic base selected from group consisting of 2,6-Lutidine, pyridine, triethylamine, diisopropylamine, and diisopropylethylamine in amount ranging from about 2.0 equivalents to about 5.0 equivalents.
14. The process as claimed in claim 2, wherein the solvent is organic solvent selected from group consisting of Toluene, ethylacetate, Diisopropyl ether and halogenated solvent selected from group comprising dichloromethane and chloroform, or any combination thereof.
15. The process as claimed in claim 1, wherein the Everolimus has purity ranging from about 85% to about 99.9%.
16. The process as claimed in claim 1, wherein the Everolimus has yield ranging from about 75% to about 99%.
17. The process as claimed in claim 1, wherein the Lewis acid is selected from group consisting of $BF_3.Et_2O$ and zinc chloride.
18. The process as claimed in claim 1, wherein the organic acid is selected from group consisting of methanesulfonic acid, p-toluene sulfonic acid, and formic acid or any combination thereof.

* * * * *